United States Patent [19]

Berci

[11] Patent Number: 4,846,153
[45] Date of Patent: Jul. 11, 1989

[54] INTUBATING VIDEO ENDOSCOPE

[76] Inventor: George Berci, 1650 San Ysidro Dr., Beverly Hills, Calif. 90210

[21] Appl. No.: 204,740

[22] Filed: Jun. 10, 1988

[51] Int. Cl.$^4$ ................................................. A61B 1/04
[52] U.S. Cl. .......................................... 128/6; 604/99
[58] Field of Search ................... 128/3, 4, 5, 6, 7, 328; 604/96, 97, 98, 99, 100, 101, 102, 103

[56] References Cited

U.S. PATENT DOCUMENTS

| | | | |
|---|---|---|---|
| 3,760,797 | 9/1973 | Stauffer | 128/6 |
| 3,788,304 | 1/1974 | Takahashi | 128/6 |
| 4,146,019 | 3/1979 | Bass et al. | 128/6 |
| 4,495,948 | 1/1985 | Shapiro | 604/99 X |
| 4,615,332 | 10/1986 | Buess et al. | 128/6 |
| 4,616,630 | 10/1986 | Arakawa | 128/4 |

Primary Examiner—William H. Grieb
Attorney, Agent, or Firm—Marvin H. Kleinberg; Matthew F. Jodziewicz

[57] ABSTRACT

An endoscope includes an elongated sheath member, with a selectively controllable bendable section which houses an image forming optical system. A generally rigid section includes a control housing. An image transmitting optical system extends throughout the length of the sheath member and terminates behind and adjacent the image forming system. A light transmitting system also extends throughout the length of the sheath member to the image forming optical system, the rearward end of which is adapted to be operatively connected to a light source. A channel, extending throughout the length of the sheath member, provides a flow of pressurized gas is directed across the image forming optical system to keep the image forming optical system operationally clear.

9 Claims, 3 Drawing Sheets

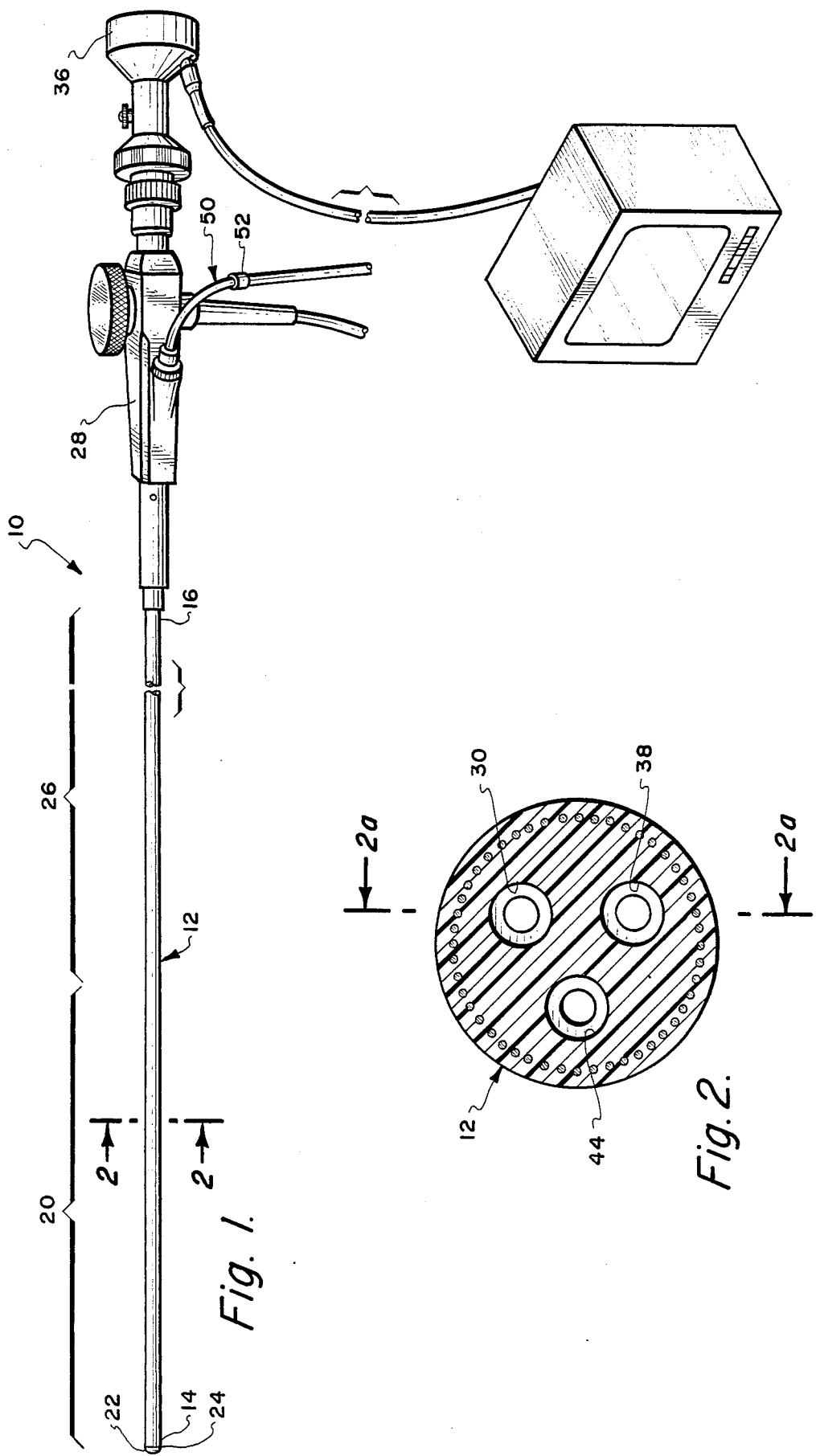

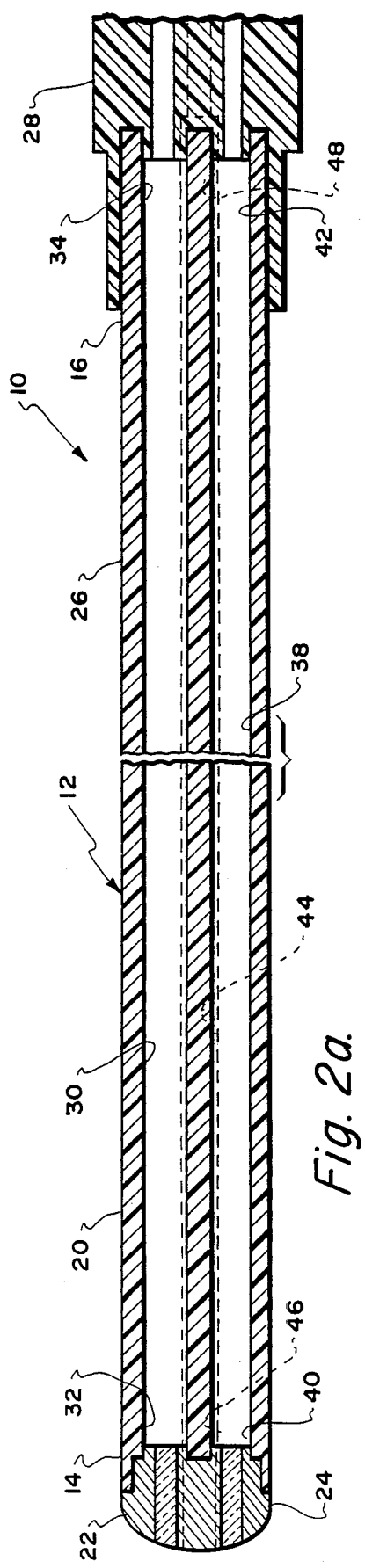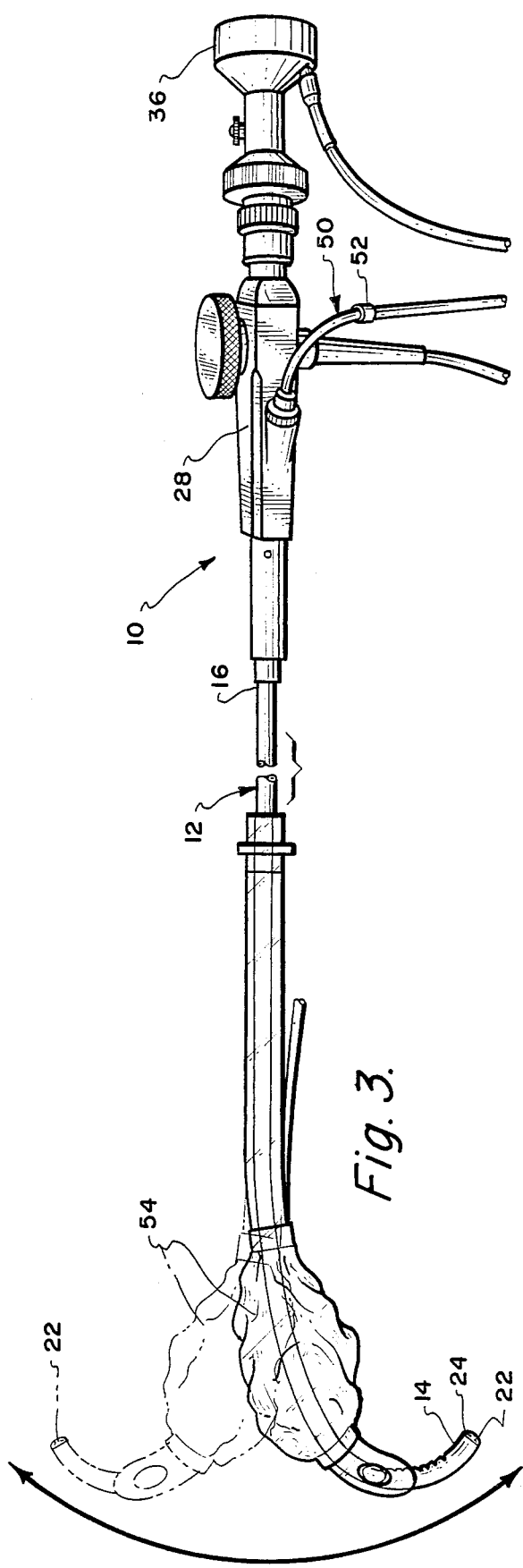

INTUBATING VIDEO ENDOSCOPE

BACKGROUND OF THE INVENTION

1. Field of the Invention

This invention relates in general to an endoscope, and, more particularly, to an endoscope having a sheath member with a controllably bendable distal or forward sheath portion and a generally rigid proximal or rearward sheath portion, which sheath member further includes an image transmitting system therethrough.

2. Description of the Related Art

When a surgical technique requires that a patient be placed under a general anesthesia, the anesthetic is usually administered to the patient by inhalation. To accomplish this, a endotracheal tube with an inflatable cuff is introduced into the patient's trachea after the patient is sedated or "put to sleep". Once the endotracheal tube is properly positioned, the cuff is inflated to seal the trachea passageway from ambient gases, and the anesthetic is introduced to the patient for inhalation through a lumen in the endotracheal tube.

When this technique is used to introduce an anesthetic, the ventilation of the patient is carefully controlled and monitored by the surgical team. The lumen in the endotracheal tube is connected to an anesthetic machine, thus forming a closed inhalation/anesthetic system between the sleeping patient and the anesthetic machine. Both the volume and cycle of the respiration of the patient during the surgical procedure is closely controlled and monitored continuously by the anesthetist.

One problem with the closed inhalation/anesthetic system technique using an endotracheal tube in association with an endoscope (which is widely used in inhalation-induced general anesthesia), is that the introduction of the endotracheal tube, that is, a plastic tube with an inflatable cuff, is not always an easy, successful or non-traumatic procedure for the patient.

Specifically, an anesthetist is usually taught that in commencing this technique, a surgical instrument, such as a laryngoscope, is first introduced into the patient's mouth and the patient's tongue is elevated so that the patient's epiglottis and vocal cords (forming the entrance to the trachea) can be visualized.

In practice, however, there are many anatomical anomalies and physical variations among patients which do not permit observation of this vital tracheal area, so that the medical practitioner attempting to perform this procedure is reduced to operating blindly, by feel, relying on his prior experience to provide him with general guidelines.

Even in the case of a "standard" intubation that proceeds without difficulties in the visualization of these vital tracheal areas, two major problems must be met and overcome by the medical practioner.

First, when the endotracheal tube approaches the patient's vocal cords, the precise location of the distal, or forward end of the endotracheal tube becomes obscured by the endotracheal tube itself. This situation requires that any further advance of the endotracheal tube through the patient's vocal cords by the medical practitioner be done semi-blindly, relying on feel.

If the endotracheal tube abrades or otherwise injures the patient's vocal cords, such inadvertent injuries can result in a number of problems ranging from a "sore throat" with transient speech impairment to a "husky voice" or even vocal cord paralysis.

Secondly, after the endotracheal tube is advanced past the vocal cords and into the patient's trachea, the distal end of the endotracheal tube should be in the range of 2 to 4 cm (about 1 to 2 inches) in front of the bifurcation of the trachea in order to ventilate both of the patient's lungs equally.

In practice, this positioning of the endotracheal tube with respect to the tracheal bifurcation is partially determined by gradation markings on the endotracheal tube itself, and by prior experience on the part of the medical practitioner. However, there are many variations in the length of the trachea of individual patients, and although such tracheal length is usually classified and determined by a patient's teeth-bifurcation distance, no absolute standard exists.

If the distal or forward tip end of the endotracheal tube is mislocated, and the patient's lungs are unequally ventilated during the general anesthesia state (half-lung ventilation), the patient may develop a post-operative pneumonia problem.

Currently, the anesthetist employs techniques such as auscultation (the process of listening for sounds emanating from the patient's chest) to determine if the patient's lungs are being ventilated equally. Such a technique as auscultation requires broad experience on the part of the practioner and some guess work, providing for a wide margin of error. Also, auscultation by the anesthetist to hear both lung excursions is not always accurate, mainly in obese patients with a large chest cavity.

The problems and complications resulting from an unsuccessful intubation attempt can be largely overcome by precise visual control of the endotracheal tube throughout the actual intubation process, that is, guiding the passage of the endotracheal tube through the patient's vocal cords and into the trachea, and, by proper positioning of the distal or forward end of the endotracheal tube in front of the patient's tracheal bifurcation so as to ventilate his lungs equally.

The following instruments and techniques of the prior art have been used to assist in the intubation process:

(1) An endotracheal tube stylet instrument which consists of a wire, generally copper, having a plastic covering. This endotracheal tube stylet is inserted into a central lumen of the endotracheal tube to straighten the natural curvature of the endotracheal tube so as to accommodate a patient having a narrow mouth.

Specifically, the distal or forward tip end of the endotracheal tube can be bent or formed by using the stylet so as to enable it to follow a shorter exterior radius, thereby facilitating the intubation of the endotracheal tube in cases requiring the elevation of an "overhanging" epiglottis.

These endotracheal tube stylets are also available with a small battery operated electric bulb located at their distal tip end that provides transillumination of the trachea.

(2) Another approach is the completely flexible fiber optic bronchoscope used in association with an endotracheal tube, siilar to that endoscope of U.S. Pat. No. 3,788,304 to Takahashi.

Completely flexible bronchoscopes were previously used for transnasal or even oral intubations. The completely flexible nature of the instrument, its extreme length, and the tiny monocular image seen in its eyepiece, all prove to be very troublesome to the anesthetist, who is not generally trained as an endoscopist.

None of the prior art techniques or instruments known to the applicant have proven to be completely successful during transnasal intubation.

While the endotracheal tube stylets appear to help, they do not avoid patient trauma, nor do they indicate the proper position and location of the patient's vocal cords.

Likewise, the completely flexible bronchoscope provides visualization of the area of concern, but due to the complete flexibility of the instrument, it becomes too flexible for easy use. Also, due to the extreme length of the completely flexible bronchoscope, the anesthetist had to be moved from his optimal position near the patient's head in the operating theater in order to accommodate the demands of the instrument.

Accordingly, none of the instruments or techniques in use today provide either an instrument or a technique which can be: reconfigured to adapt to the anatomy of an individual patient; convenient for the anesthetist who has to be located near to the patient's head; provides an enlarged image of the patient's anatomical features; incorporates both a flexible and a rigid section; or, allows sufficient ventilation or oxygenation of the patient during the intubating process.

The present invention overcomes the above described disadvantages and problems of the prior art and provides a safer and less traumatizing instrument for the intubation of a patient.

SUMMARY OF THE INVENTION

An object of the present invention is to provide a novel and useful endoscope in which the above described disadvantages and problems of the prior art are avoided.

Another object of the present invention is to provide a novel and useful endoscope which is positioned in the lumen of an endotracheal tube. The distal or forward tip end portion of the endoscope and the surrounding endotracheal tube can be precisely located and afford the practitioner a clear and enlarged visualization of the patient's anatomical features.

To achieve these objects, as well as other objects described below, the endoscope constructed in accordance with the present invention has an elongated sheath member having distal, or forward, and proximal, or rearward, ends, which is adapted for introduction into a body cavity.

The sheath member has, at its distal or forward end, a first, selectively controllable bendable section which houses an image forming optical system.

Likewise, the sheath member has at its proximal or rearward end, a generally rigid section which includes a control housing. An image transmitting optical system extends throughout the length of the sheath member in one of the lumens thereof. The forward end of the image transmitting system is operatively located behind and adjacent an image forming system in another of the lumens, while the rearward end thereof terminates in the control housing.

This arrangement permits the image of an object that is formed by the image forming optical system on the forward end of the image transmitting optical system and transmitted therethrough to the rearward end thereof, to be viewed in the proximal or rearward end portion of the sheath member.

A light transmitting system also extends throughout the length of the sheath member in another of the lumens. The forward end of the light transmitting system is operatively located adjacent the image forming optical system, and the rearward end thereof terminates in the control housing. The rearward end is adapted to be operatively connected to a light source for providing illumination of the area observed by the image forming optical system.

A channel or passageway extends throughout the length of the sheath member in another of the lumens. The forward end of the channel is operatively located adjacent the image forming optical system and has its rearward end terminating in the control housing. The channel is adapted to be operatively connected to a selectively controllable source of pressurized gas, preferably oxygen, for diffusion oxygenation of the patient undergoing intubation.

Gas flow directing means are operatively connected to the forward end of the channel for applying a flow of pressurized gas across the image forming optical system to keep the optical system clear during operation as well as to provide for a continuous controlled flow of oxygen into the patient's lungs. Controlling means in the control housing are operatively connected to a first, selectively controllable bendable section of the sheath member, for manipulating the distal or forward tip end portion of the sheath member.

When the endoscope with the surrounding endotracheal tube is successfully guided to the optimal location, just above the tracheal bifurcation, the endotracheal tube is held in place and the endoscope is withdrawn. Th cuff is then inflated and oxygen and other gases can be supplied to the patient under control of the anesthetist.

The novel features of construction and operation of the invention will be more clearly apparent during the course of the following description, reference being had to the accompanying drawings wherein has been illustrated a preferred form of the device of the invention and wherein like characters of reference designate like parts throughout the drawings.

BRIEF DESCRIPTION OF THE DRAWINGS

FIG. 1 is a perspective view of an endoscope constructed in accordance with the present invention;

FIG. 2 is an enlarged partial view of the distal end of the endoscope shown in FIG. 1;

FIG. 2a is an enlarged cross-section view taken on line 2a-2a of FIG. 2;

FIG. 3 is a view similar to that of FIG. 1 showing the endoscope of FIG. 1 in association with an endostracheal tube having an inflatable cuff.

BRIEF DESCRIPTION OF THE PREFERRED EMBODIMENT

Figure 4:
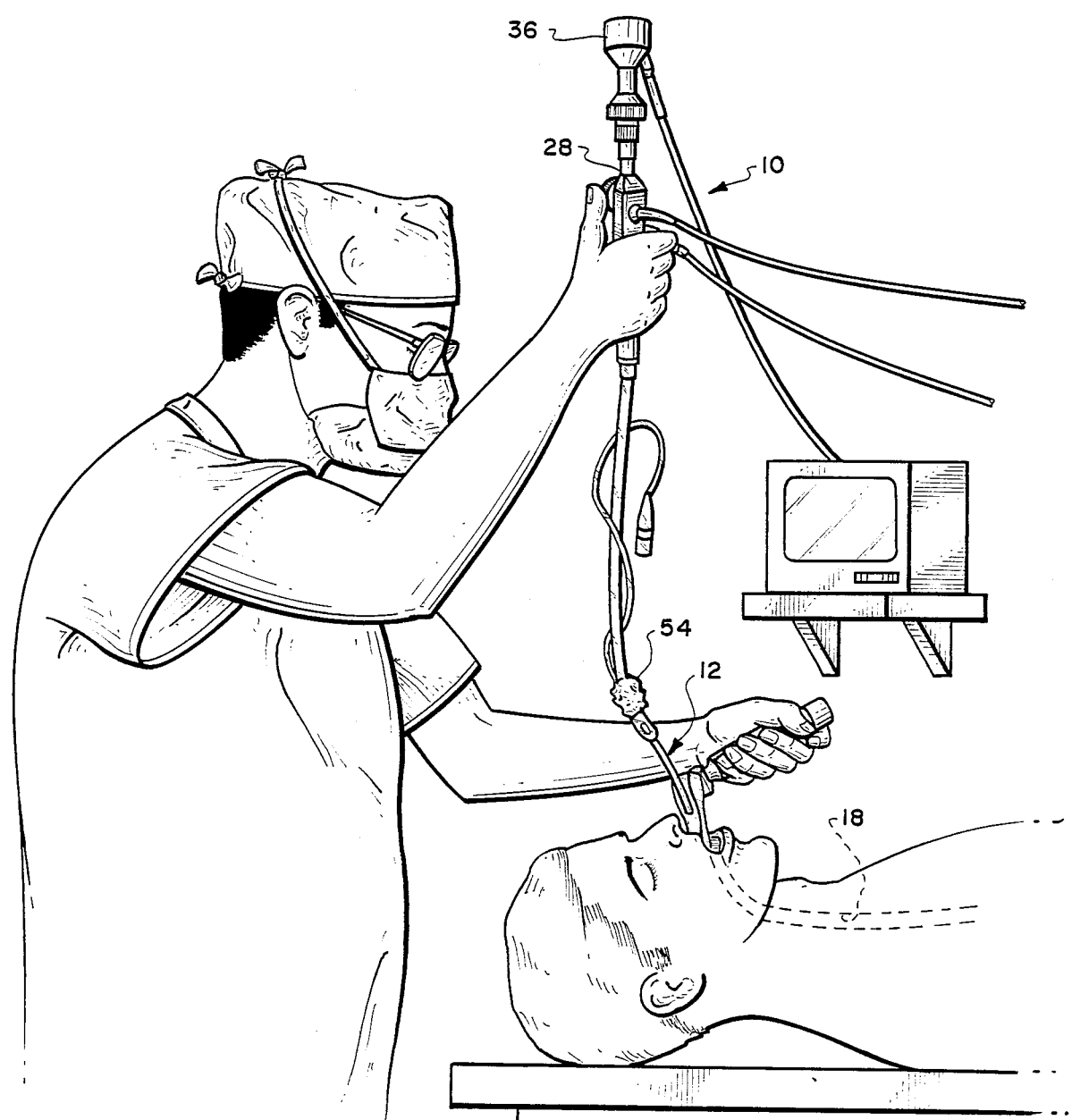
FIG. 4 is a view showing an endoscope constructed in accordance with the present invention as it would be used for insertion into a narrow passage of a body cavity such as the human trachea.

Referring to FIGS. 1 through 3 showing an endoscope constructed in accordance with the present invention, it is seen that the endoscope 10 comprises an elongated sheath member 12 having distal or forward and proximal or rearward ends 14, 16 respectively. Sheath member 12 has a cross-sectional shape, as suggested in FIGS. 2 and 2a, that is adapted for introduction of the endoscope 10 into a body cavity 18 as shown in FIG. 4.

At the distal or forward tip end 14 of the sheath member 12, is a first, selectively controllable bendable section 20, having a length about one-third the overall length of the sheath member 12. This is an important aspect of the invention and is described further below.

Bendable and flexible section 20 houses an image forming optical system 22 at its far end 24. While an image forming system using fiber optics is described herein, new advances, such as the self-contained integrated circuit chips that act as cameras, may be substituted for the fiber optics systems described herein.

At the proximal or rearward end 16 of the sheath member 12, is a generally rigid section 26 which includes a control housing 28. This section 26 acts to provide a directional guide for the endoscope 10.

An image transmitting optical system 30 extends through the sheath member 12, and has forward and rearward ends 32, 34 respectively. The forward end 32 of the image transmitting system 30 is operatively located behind and adjacent the image forming system 22. The rearward end 34 thereof terminates in the control housing 28 and is adapted to be operatively connected to a video system 36 for viewing the image of an object on a television monitor.

The image transmitting optical system 30, as configured in this preferred embodiment, permits an image of an object that is viewed by the image forming optical system 22 at the forward end 32 of the image transmitting optical system 30 to be transmitted therethrough to the rearward end 34 thereof, to be converted at the proximal end portion 16 of the sheath member 12 for transmission to and viewing on the television monitor. Video recording means (not shown) can be operatively connected in a preferred embodiment by attachment of the eyepiece to a small television camera to receive and record onto a recording medium such as video tape.

A light transmitting system 38 extends through the sheath member 12, and has forward and rearward ends 40, 42 respectively. The forward end 40 of the light transmitting system is operatively located adjacent the image forming optical system 22. The rearward end 42 thereof terminates in the control housing 28 and is adapted to be connected to a light source (not shown) for providing illumination to the image forming optical system 22.

A gas channel or passageway 44 extends through the sheath member 12, and has forward and rearward ends 46, 48 respectively. The forward end 46 of the channel 44 is operatively located adjacent the image forming optical system 22, while the rearward end 48 thereof terminates in the control housing 28, and is adapted to connect to a selectively controllable source of pressurized gas (not shown).

Gas directing means 50, at the forward end 46 of the channel 44 applies a flow of pressurized gas across the image forming optical system 22 for keeping the optical system 22 operationally clear during the intubation procedure.

Channel 44 provides a passageway for the anesthetist to provide an oxygen in-flow (generally in the range of about 4 to 6 liters per minute) to the patient undergoing the intubation procedure. This oxygen in-flow serves two purposes: first, it is directed across the image forming optical system 22 to defog or maintain system 22 clear; and, secondly, to provide diffuse oxygenation (that is, to inject oxygen into the patient's lungs) so as to wash out carbon dioxide ($CO_2$) and Ox diffusion of the patient during the intubation procedure. This later aspect of the invention is an important safety measure during intubation, as a patient's life can be maintained by diffusion oxygenation for periods of 2 to 3 minutes without outside breathing.

Manipulating means 54 are operatively connected to the first, selectively controllable bendable section 20 of the sheath member 12 from at the control housing 28 for manipulating the distal or forward tip end portion 14 of the sheath member 12.

It is preferable that the forward tip end section 14 of the sheath member 12 have a dual wide radius of curvature, and a deflection in one direction (upward) of about 160 degrees, and an opposite second direction deflection of about 100 degrees.

Various means are known and customarily used in the art, for example, U.S. Pat. No. 3,788,304 to Takahashi. All such means are applicable for use with the present invention and may, by appropriate modification, be incorporated hereinto.

In an alternate embodiment of an endoscope constructed in accordance with the present invention, additional channels or lumens may be provided throughout the sheath member for such purposes as additional gas passageways or channels for transporting instruments to selected locations within the body cavity which are visualized and located using the imaging provided in the present invention.

In general, it is seen from both the above description of a preferred embodiment of an endoscope constructed in accordance with the invention and the description of the method of operation that follows, that the proportion or ratio between the lengths of the flexible section 20 and the generally rigid section 26, is an important aspect of the present invention.

This is because when the endotracheal tube is associated with the endoscope 10, as shown in FIGS. 3 and 4, the length of the flexible section 20 that protrudes from the endotracheal tube must be capable of variation to accommodate a patient's particular anatomy.

After a period of experimentation, it was determined that to provide an optimal instrument for general use among a wide variety of patients, the flexible portion 20 of the sheath member 12 should be in the range of about 5 to 21 centimeters, while the overall length of the rigid portion 26 should be in the range of about 10 to 30 centimeters.

Also, the preferred length of the sheath member 12 is about 35 centimeters overall, and that of the associated endotracheal tube to be about 30 centimeters overall. While these figures may vary, it is essential that the length ratios of the individual parts permits the user to adjust the flexible section 20 protruding from the endotracheal tube to accommodate the particular anatomy of the patient.

An adjustable locking collar, secured by a screw or the like, that is selectively releasable, can be associated with the sheath member 12 of the endoscope 10, and the endotracheal tube as is shown in FIGS. 3 and 4, to hold the desired relationship once it is chosen by the user.

In use, a standard endotracheal tube is placed over the sheath member of the endoscope prior to commencing the intubation process as shown in FIG. 3. The light transmitting system of the endoscope is connected to a light sourceto provide illumination for the imaging system of the endoscope.

The internal gas passage channel of the endoscope is connected to a source of controlled pressurized gas, such as oxygen. Finally, the viewing eyepiece section of the endoscope is connected to a video system, such as one including a small television camera, for both recording and displaying the transmitted image for the attending anesthetist. The display of the image can be done on a miniature, preferably color, television monitor that can be located in a location convenient for the anesthetist.

By displaying an enlarged transmitted image on a video monitor, two immediate benefits over prior art instruments are achieved. First, the enlarged view of the patient's anatomical details assists the anesthetist in identifying the location of the forward tip end of the endoscope. Secondly, the anesthetist is offered a binocular view of the area of interest as opposed to the miniature, monocular view afforded him by prior art instruments employing only a fiber optics imaging system.

While observing the image displayed with the present invention, the anesthetist introduces the distal end of the endoscope into the patient's mouth and manipulates the bending of the distal end portion of the sheath member of the endoscope to accommodate the encountered anatomy of the patient. Due to the controllable bending of the distal or forward tip end of the endoscope, the distal or forward tip end portion of the endoscope can be carefully maneuvered through the patient's body cavity minimizing or even eliminating patient trauma.

When the patient's vocal cords are visualized, the distal end of the endoscope and the endotracheal tube can be carefully advanced through this delicate structure with ease and without inducing patient trauma. Entering the patient's trachea, the endoscope and the endotracheal tube are advanced until the bifurcation of the trachea is visualized. At this stage of the intubation process, further advancement of the endoscope is stopped and the thumb control is released on the bendable distal portion of the endoscope sheath member.

With the endoscope properly positioned, the position of the endotracheal tube is adjusted toward the distal end of the endoscope until it is properly located in the patient's trachea. At this point, the endoscope cab be withdrawn from the patient's trachea through the endotracheal tube. The endotracheal tube is left in position and is connected to the inhalation anesthetic machnery. The cuff of the endotracheal tube is then inflated to hold the tube in place and to seal the airways external to the tube.

While the endoscope is being advanced through the patient's vocal cords and trachea, positive pressure is supplied by a gas, such as oxygen, through the gas passageway channel of the endoscope. This continues ventilation and insufflation of the patient so as to ensure diffusion oxygenization, even in the paralyzed (respiration paralysis induced by the anesthetist) patient, as well as to prevent fogging of the imaging system of the endoscope.

Finally, the entire intubation process may be video taped or otherwise recorded on a recording medium for documentation purposes, including further study or teaching.

The invention described above is, of course, susceptible to many variations, modifications and changes, all of which are within the skill of the art. It should be understood that all such variations, modifications and changes are within the spirit and scope of the invention and of the appended claims. Similarly, it will be understood that it is intended to cover all changes, modifications and variations of the example of the invention herein disclosed for the purpose of illustration which do not constitute departures from the spirit and scope of the invention.

What is claimed is:

1. An endoscope comprising:
    (a) an elongated sheath member having distal and proximal ends adapted for introduction into a body cavity and having at its distal end, a first, selectively controllable bendable section housing an image-forming optical system, and, at its proximal end, a generally rigid section including a control housing, the ratio between said first, selectively controllable bendable section and said generally rigid section being approximately one-third to two-thirds;
    (b) an image transmitting optical system extending through said sheath member, said image transmitting optical system having forward and rearward ends, the forward end of said image transmitting system operatively located behind and adjacent said image forming system and the rearward end thereof terminating in said control housing, thereby permitting an image of an object adjacent said distal end to be viewed in said proximal end portion;
    (c) a light transmitting system extending through said sheath member, said light transmitting system having forward and rearward ends, the forward end of said light transmitting system operatively located adjacent said image forming optical system and the rearward end thereof terminating in said control housing and adapted to be operatively connected to a light source for providing illumination for said image forming optical system;
    (d) a channel extending through said sheath member, said channel having forward and rearward ends, the forward end of said channel operatively located adjacent said image forming optical system and the rearward end thereof terminating in said control housing and adapted to be operatively connected to a selectively controllable source of pressurized gas;
    (e) means operatively connected to the forward end of said channel for directing a flow of pressurized gas across said image forming optical system for keeping said image forming optical system operationally clear; and
    (f) control means in said control housing operatively connected to said first selectively controllable bendable section of said sheath member for manipulating said distal end portion of said sheath member to permit selective manipulation of said distal end portion of said sheath member through a patient's tracheal anatomy.

2. An endoscope as recited in claim 1 wherein said rearward end of said image transmitting system is adapted to be operatively connected to a small video camera system for viewing an object image on a television monitor.

3. An endoscope as recited in claim 1 further including video recording means operatively connected to said rearward end of said image transmitting system for recording said transmitted object images onto a recording medium.

4. An endoscope as recited in claim 1 wherein said means for directing a flow of pressurized gas across said image forming optical system comprises a nozzle adapted to selectively direct the discharge of said flow of pressurized gas from said channel across said image forming optical system.

5. An endoscope as recited in claim 1 wherein the length of said selectively controllable bendable section of said sheath member is in the range of 5 to 21 centimeters and the overall length of said sheath member is about 35 centimeters.

6. An endoscope comprising:
an elongated sheath member having distal and proximal ends adapted for introduction into a body cavity and having at its distal end a first selectively controllable bendable section having a length about one-third the overall length of said sheath member, said section housing an image forming optical system, said sheath member having at its proximal end a generally rigid section including a control housing;
an image transmitting optical system extending through said sheath member, said image transmitting optical system having forward and rearward ends, said forward end being operatively located behind and adjacent said image forming system, and said rearward end terminating in said control housing, said optical system being adapted to be operatively connected to a video system for viewing a transmitted image of an object on a television monitor, thereby permitting an object image formed by said optical system on the forward end of said optical system and transmitted to the rearward end to be viewed in both said proximal end portion and on a television monitor;
video recording means operatively connected to said rearward end of said optical system for recording said the transmitted image of an object onto a recording medium;
a light transmitting system extending through said sheath member, said light transmitting system having forward and rearward ends, said forward end operatively located adjacent said image forming optical system, and said rearward end terminating in said control housing, said light transmitting system being adapted to be operatively connected to a light source for providing illumination for objects to be visualized by said image forming optical system;
a channel extending through said sheath member, said channel having forward and rearward ends, said channel forward end being operatively located adjacent said optical system, said channel rearward end terminating in said control housing and adapted to be operatively connected to a selectively controllable source of pressurized gas;
gas control means, including a directional nozzle member, operatively connected to said channel forward end for directing a flow of pressurized gas across said optical system to keep said optical system operationally clear; and
control means operatively connected to said first selectively controllable bendable section for manipulating said distal end portion of said sheath member.

7. An intubation process using an endoscope with an intubating sheath member having both flexible and and rigid sections and said endoscope further having a video imaging system connected to video monitoring and display means and a channel for applying a gas to the distal end of the endoscope, in association with an endotracheal tube having an inflatable cuff, the process comprising the steps of:
(1) placing the endoscope through the central lumen of the endotracheal tube;
(2) inserting the distal end of the endoscope into the oral cavity of a subject;
(3) using the video imaging system and the video monitoring means, positioning the distal end of the endoscope through the larynx to a selected location near the tracheal bifurcation;
(4) using the video imaging system and the video monitoring and display means, guiding the endotracheal tube over the endoscope toward the distal end of the endoscope to issure that the distal end of the endotracheal tube does not extend beyond that of the endoscope;
(5) inflating the inflatable cuff to hold the endotracheal tube in position; and
(6) withdrawing the endoscope from the trachea and the central lumen of the endotracheal tube.

8. An intubation process as recited in claim 7 further including the step of:
applying a gas to the channel and directing the gas exiting from the channel across the video imaging system to keep the video imaging system clear.

9. An intubation process as recited in claim 7 further including the step of:
applying and controlling a gas flow through the channel to ensure diffusion oxygenation of said subject during the intubation process.

* * * * *